United States Patent [19]

Sekiguchi

[11] Patent Number: 5,287,732
[45] Date of Patent: Feb. 22, 1994

[54] ROTARY VISCOSIMETER

[75] Inventor: Koji Sekiguchi, Tokyo, Japan

[73] Assignee: Toki Sangyo Co., Ltd., Tokyo, Japan

[21] Appl. No.: 859,466

[22] PCT Filed: Oct. 3, 1991

[86] PCT No.: PCT/JP91/01337

§ 371 Date: Jun. 2, 1992

§ 102(e) Date: Jun. 2, 1992

[87] PCT Pub. No.: WO92/06365

PCT Pub. Date: Apr. 16, 1992

[30] Foreign Application Priority Data

Oct. 3, 1990 [JP] Japan ............... 2-265715

[51] Int. Cl.⁵ .......................................... G01N 11/14
[52] U.S. Cl. ................................. 73/54.33; 73/54.35
[58] Field of Search ................. 73/54.33, 54.35, 54.32, 73/54.28, 54.23

[56] References Cited

U.S. PATENT DOCUMENTS 3,886,789  6/1975  Brookfield .................... 73/54.35

FOREIGN PATENT DOCUMENTS 26195     8/1970  Japan ................... 73/54.32
231549    9/1990  Japan ................... 73/54.35
2-247540 10/1990  Japan .
972328   11/1982  U.S.S.R. ............... 73/54.35
2204701  11/1988  United Kingdom ....... 73/54.28

Primary Examiner—Hezron E. Williams
Assistant Examiner—Joseph W. Roskos
Attorney, Agent, or Firm—Lowe, Price, LeBlanc & Becker

[57] ABSTRACT

A rotary viscosimeter has a control mode for measuring the viscosity of a liquid by a spring relaxation method and a control mode for measuring the viscosity by rotating a rotor 6a at a constant speed. In this rotary viscosimeter, a driving power is transmitted from a driving power source to a rotor shaft 5b via a spring 4a for rotating the rotor 6a. The rotor shaft 5b is supported on a pivot 11 and a bearing 12. When the viscosity is measured by the spring relaxation method, locking of the rotor shaft 5b is released after the spring 4a is biased while the rotor shaft 5b has been locked. When measurement of the viscosity is performed by rotating the rotor 6a at a constant speed, the rotor 6a is rotated while the locking of the rotor shaft 5b is released. When measurement is not being performed, the rotor shaft 5b is locked and the pivot 11 is separated from the bearing 12.

13 Claims, 14 Drawing Sheets

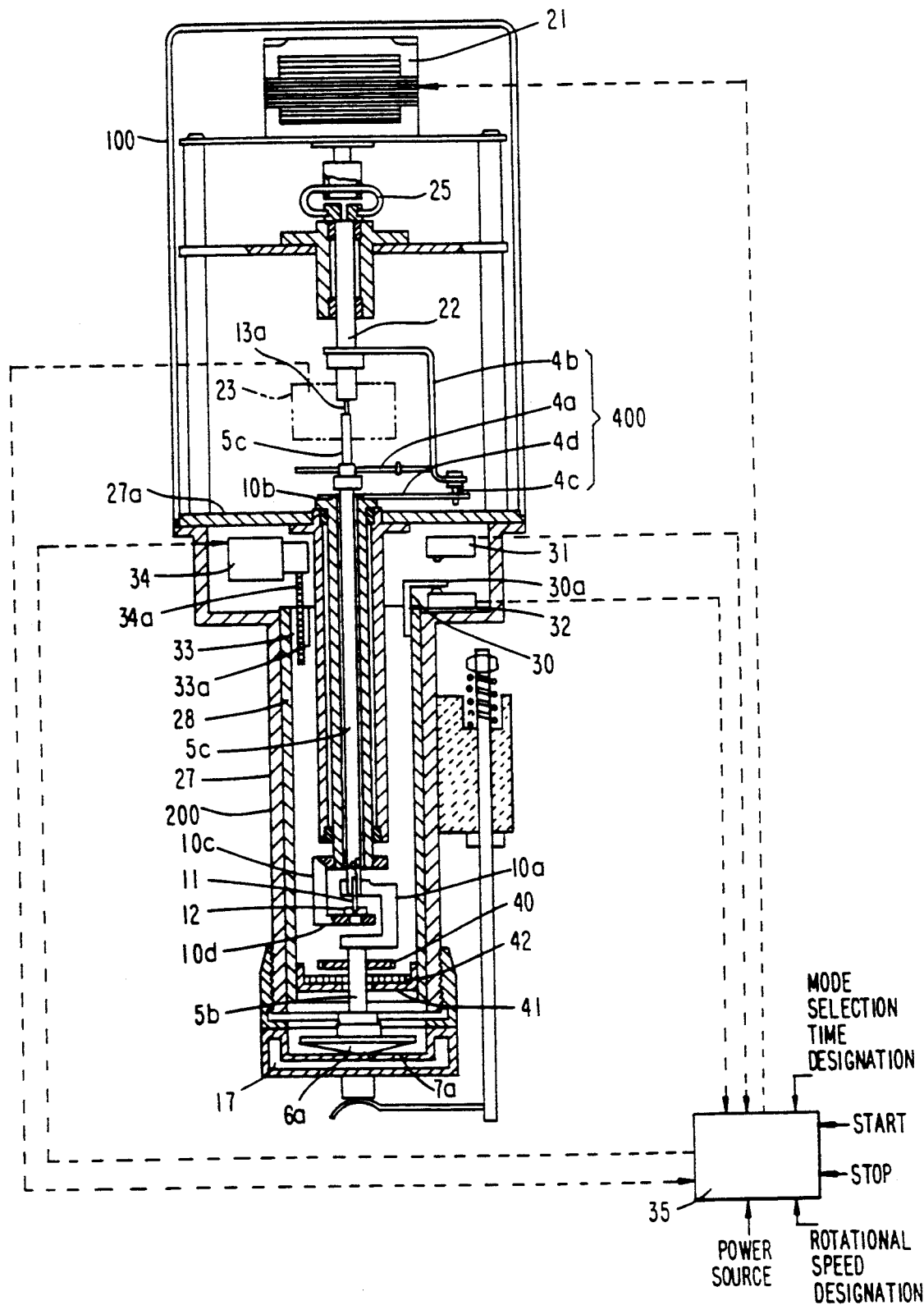

PIVOT IS SEPARATED
FROM BEARING

PIVOT IS IN
CONTACT WITH
BEARING

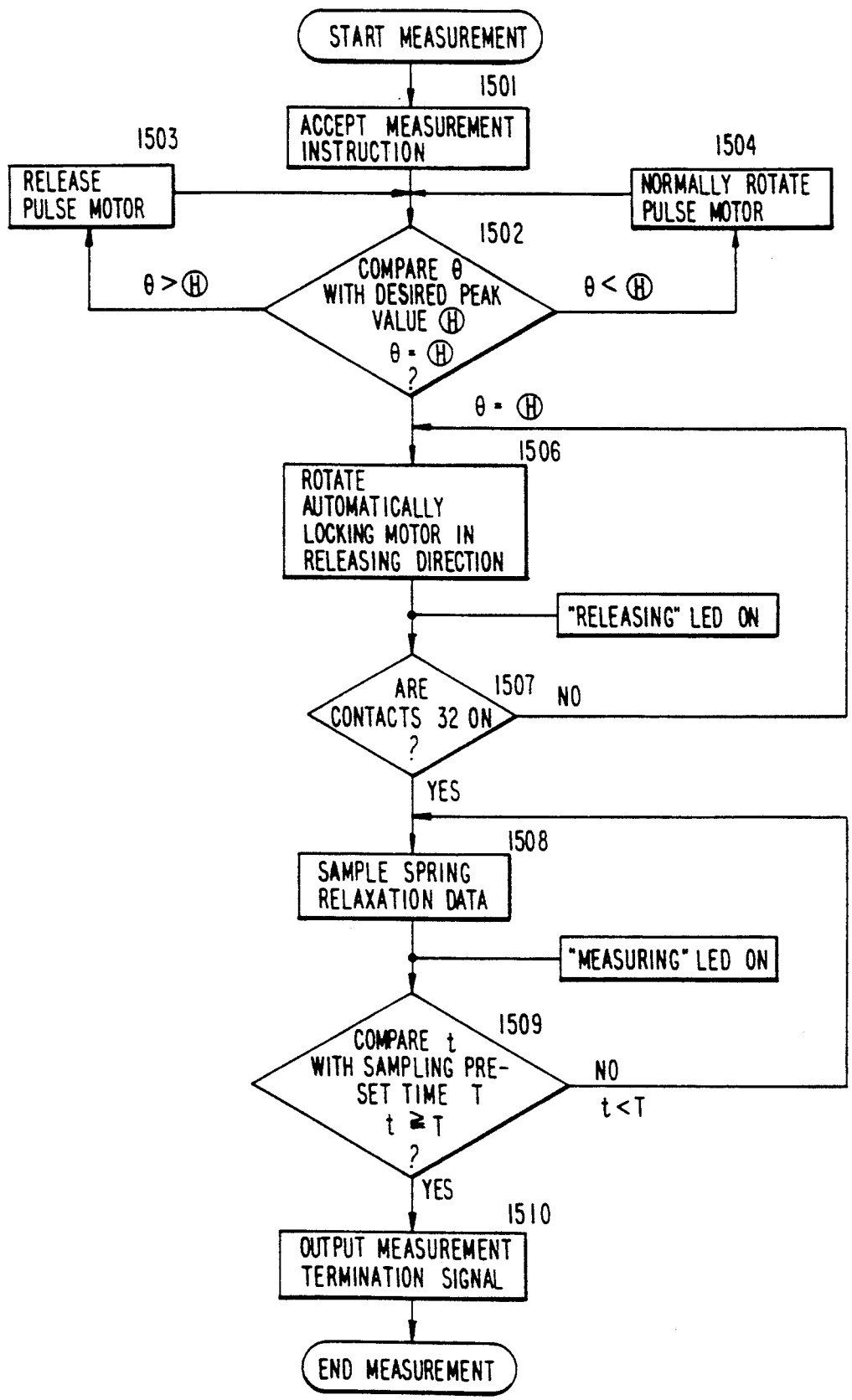

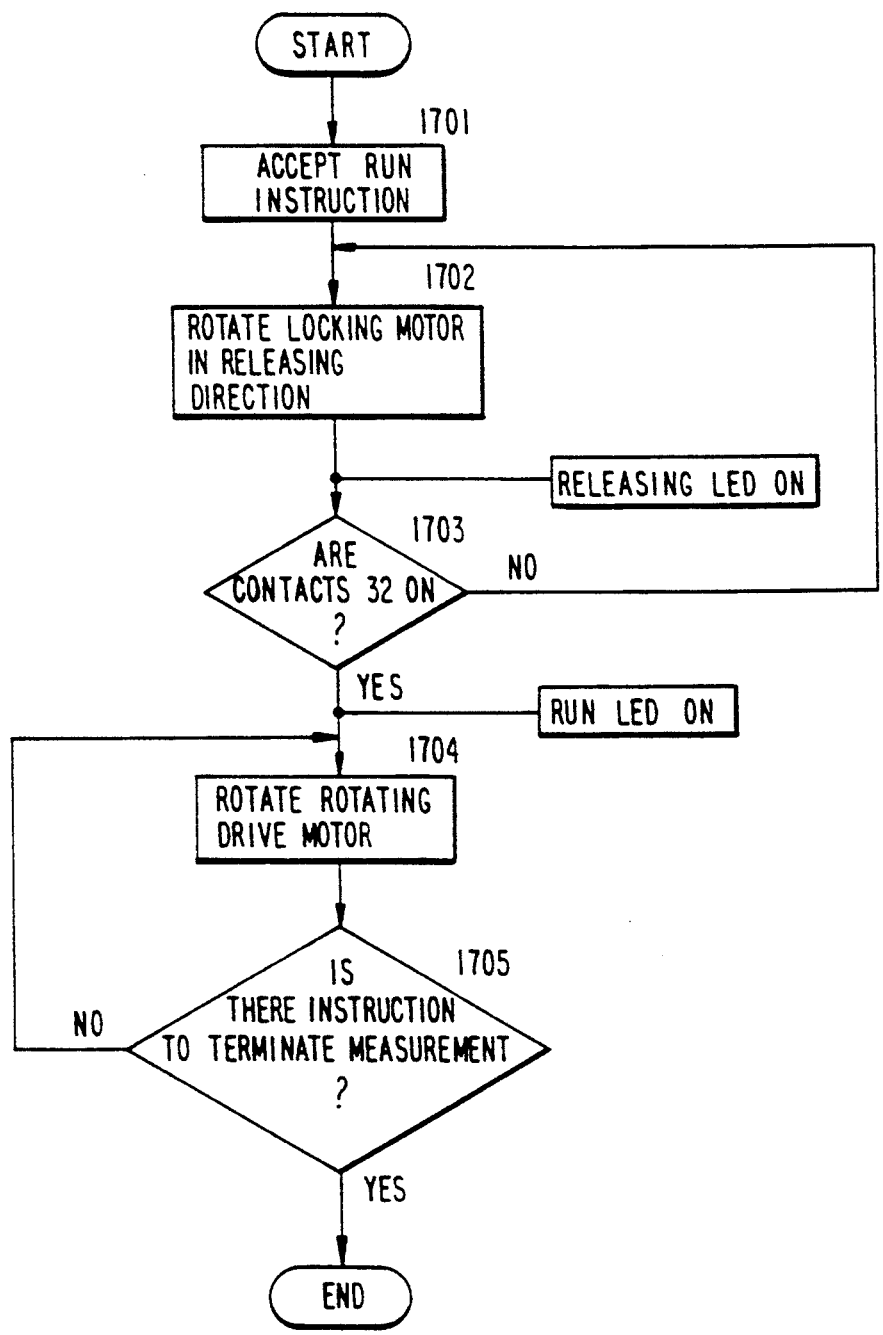

ROTARY VISCOSIMETER

FIELD OF THE INVENTION

The present invention relates to a rotary viscosimeter for measuring the viscosity of a liquid by bringing a rotor into contact with the liquid, and rotating the rotor via a spring, and in particular to a rotary viscosimeter which is capable of automatically measuring the viscosity characteristics by using a spring relaxation technique in an ultra-low fluid viscosity range.

BACKGROUND OF THE PRIOR ART

A rotary viscosimeter which measures the viscosity characteristics of a sample liquid in an ultra-low fluid viscosity range by using the relaxation of a spiral spring is disclosed in a report entitled "A new method for the viscosity measurement of paint in setting, sagging, levelling and penetration shear rate range of 0.001 to 1.0 reciprocal seconds using a cone/plate spring relaxation technique", by T. C. Patton, Journal of paint technology, Vol. 38, No. 502, November 1966. This viscosimeter is a multi-purpose rotary viscosimeter having a cone/plate rotor in a measuring unit (Wells-Brookfield micro viscometer RTV cone plate model).

The summary of the structure of such a viscosimeter is shown in FIG. 4. The viscosimeter includes a scale disc 3 secured to a drive shaft 2 which is rotated by a driving motor 1 with a reduction gear. A rotor shaft 5 is connected with the lower end 21 of the drive shaft 2 via a spring 4. A sample liquid 9, the viscosity of which is to be measured, is disposed between a cone rotor 6 and a plate 7 below the lower end of the rotor shaft 5. This condition is enlarged and shown in FIG. 5.

On the other hand, a pointing needle 8 which extends above the scale disc is secured to the rotor shaft 5 so that the relative angular displacement between the drive shaft 2 and the rotor shaft 5 can be read from the position of the pointing needle 8 on the scale disc 3. If the torsional spring constant of the spring 4, the size of the rotor 6 and the rotational speed of the rotor are determined, the scale pointed to by the needle 8 on the scale disc 3 is proportional to the viscosity of the sample liquid. Accordingly, the viscosity can be determined from the scale pointed to by the needle 8.

In the description of the operation principle of the viscosimeter set forth in the above mentioned report, it is assumed that the rotor shaft 5, the rotor 6 and the pointing needle 8 are engaged with the lower end 21 of the drive shaft. However, the system of the rotor shaft 5 is unstable in such a structure. Accordingly, in an actual viscosimeter, the rotor shaft 5a is borne by a pivot 11 and a bearing 12 made of gemstone as shown in FIG. 6 so that the upper end of the rotor shaft 5a is prevented from swinging by a pin 13 penetrating into a hole in the shaft. The other parts are represented with reference numerals suffixed with a of the corresponding parts in FIG. 4. However, 4a corresponding to the spring 4 in FIG. 4 denotes a spiral spring. 17 denotes a jacket for maintaining the sample liquid at a constant temperature, to which circulating water is introduced from a separately provided constant temperature bath.

Since both the pointing needle 8a and the scale disc 3a are rotating during measurement of the viscosity in the present viscosimeter, it is hard to read the scale pointed to by the needle during the rotation of these parts. Accordingly, standard operation of the present viscosimeter is performed as follows: After the indicated point or the scale has become stable after starting the rotation of the viscosimeter, a clamp lever 14 of FIG. 6 is depressed downward with a finger to push up a push-up chip 15 around a fulcrum 14'. This causes a scale disc shaft 16 engaged with the push-up chip 15 and the scale disc 3a linked with the shaft 16 to be lifted upward. As a result of this, the pointing needle 8a is clamped relative to the scale disc 3a to keep the scale position while the pointing needle 8a is engaged with one of a number of knurled grooves (not shown) formed on the outer periphery of the scale disc 3a and is rotated together therewith.

The pointing needle 8a is stopped while clamped on the scale disc 3a when the motor is stopped in this state. Accordingly, the scale pointed to by the pointing needle can be easily read. When the clamp lever 14 is released, the pointing needle is disengaged from the scale disc 3a so that the pointing needle 8a is released to return to the "0" position on the scale disc.

The above-mentioned report teaches a viscosity measurement by a spring relaxation method using the relaxation of a spiral spring in the above mentioned viscosimeter. In the viscosity measurement using the spring relaxation technique, the rotor is manually rotated until the spiral spring of the viscosimeter assumes a full scale position (in which the pointing needle points to "100" on the scale). This operation is carried out without a measuring unit installed, and before the sample liquid is loaded between the coil and the plate so that the pointing needle is clamped in this position. Winding of the spiral spring is conducted by manually and slowly rotating the rotor at the lower end thereof until the pointing needle points to "100" on the scale. In order to fix the pointing needle in this position, i.e. to fix the spiral spring in the wound condition, the clamp lever is fixed in the depressed position, for example, by winding a rubber band around the lever after depressing the clamp lever. Thereafter, this condition is maintained until the lever is released for performing the actual viscosity measurement. Subsequently, the viscosity measurement is performed by the following steps.

A stopwatch is set to zero and the lever which fixes the pointing needle at "100" on the scale is released. Simultaneously with this, the stopwatch is started. Then, the point on the scale which is indicated by the needle is read at appropriate intervals (for example, at intervals of 10 to 15 seconds at the start of the measurement cycle and at intervals of 30 seconds near the end). The measurement is completed over several minutes. The measurement is terminated when the change in reading since the previous reading becomes less than the minimum scale division.

Then, the thus obtained data are plotted on semilogarithmic graph paper. The readings are plotted on the logarithmic scale (two cycles) and the time data are plotted on linear scale.

The resultant curves are exemplarily illustrated in FIG. 7. The viscosity at a desired point on the curve, the shear stress corresponding to this point and the rate of shear are determined as follows:

The shear stress is determined from a coordinate value on the logarithmic axis, through which a horizontal straight line is drawn leftward from a point to be determined. The reading is proportional to the shear stress and can be converted into the shear stress represented in $dyne/cm^2$ by multiplying it by an appropriate constant.

If the maximum torque (corresponding to the full scale 100) of the spiral spring of the viscosimeter is represented by $M_{100}$, the torque Ms relative to the desired scale S is represented by a formula (1).

$$Ms = (S/100)M_{100} \qquad (1)$$

As shown in the enlarged view of the cone rotor portion of FIG. 5, the relation between the shear stress applied upon the sample liquid loaded between the rotating cone of the viscosimeter and the stationary plate and the torque M applied upon the cone is represented by a formula (2).

$$\tau(\text{shear stress}) = 3M/2\pi r^3 \qquad (2)$$

wherein r denotes the radius of the cone. A formula (3) is obtained by putting the formula (1) into the formula (2).

$$\tau s = 3(S/100)M_{100}/2\pi r^3 \qquad (3)$$

wherein $\tau$ s is the shear stress applied upon the sample liquid when the point on the scale is S.

A case in which the pointing needle is preliminarily clamped in the position of the scale S is firstly considered. Although a torsional reaction force of the spiral spring is applied upon the rotor in this phase, the rotor is prevented from rotating by a clamp mechanism. When clamping of the rotor is released on starting the measurement (t=O), the spiral spring is relaxed so that the rotor commences rotating.

If the change in the indicated point on the scale during a very short period of time dt is represented as ds, a very small angle $d\theta$ (in radian) by which the pointing needle is moved during the period of time dt is represented by formula (4).

$$d\theta = (ds/C)2\pi \qquad (4)$$

wherein constant C denotes the full scale value which is obtained by dividing by 360 at the same graduation pitch at which the scale reads 100 on the scale plate of the viscosimeter.

If the rotational angular speed of the pointing needle at the desired time is represented as radian/second, $\omega = d\theta/dt$. A formula (5) is obtained if d in the formula (4) is converted into this representation.

$$\omega = d\theta/dt = (ds/dt)(2\pi/C) \qquad (5)$$

The shear rate D is represented by a formula (6) in consideration of the shape of the cone in the cone/plate viscosimeter.

$$D = \omega/\alpha \qquad (6)$$

wherein $\omega$ and $\alpha$ denote the rotational angular velocity and the angle of the cone, respectively.

A formula (7) is obtained by putting $\omega$ in formula (5) into formula (6).

$$D = (ds/dt)(2\pi/C\alpha) \qquad (7)$$

The viscosity $\eta$ of the sample liquid is defined as the ratio of the shear stress to the shear rate. In other words, the basic formula of the viscosity is given by a formula (8).

$$\eta(\text{viscosity}) = \tau(\text{shear stress})/D(\text{shear rate}) \qquad (8)$$

A formula (9) is obtained by putting D in formula (7) and in $\tau$s formula (3) into formula (8) and by rearranging it.

$$ds/S = (3M_{100}C\alpha/4\pi^2 r^3 100\eta)dt \qquad (9)$$

From (9), $$d\ln S = (3M_{100}C\alpha/4\pi^2 r^3 100\eta)dt$$

$$\eta = (3M_{100}C\alpha/4\pi^2 r^3 100)/(d\ln S/dt) \qquad (10)$$

Since the values in the parentheses are determined by the graduation dividing specification of the full scale torque scale plate of the spiral spring in the viscosimeter, the cone size, and the angle, they are determined by the design of the viscosimeter. Accordingly, the formula (9) can be simplified as represented by formula (11).

$$K = 3M_{100}C\alpha/4\pi^2 r^3 100.2.3$$

$$\text{-}\eta = K/(d \log S/dt) \qquad (11)$$

From the formula 11, the viscosity at a desired point on the curve which is obtained as shown in FIG. 7 is obtained by drawing a straight line which is tangential to that point. The viscosity $\eta$ can be determined by the calculation based upon the in proportional relation of the viscosity with the gradient d log S/dt as is given by the formula 11. The shear stress $\tau$s and the shear rate D in this point can be determined by the relations set forth in formulae (3) and (8), respectively. The values which are determined from the dimensions of the viscosimeter and the measurement data in such a manner are set forth in FIG. 7.

The foregoing is the gist of the above-mentioned report. When the viscosity measurement using the spring relaxation technique is performed in the above mentioned conventional art, the clamp lever should be fixed by a rubber band in order to clamp the pointing needle by preliminarily manually rotating a rotor so that the spiral spring is wound to a full scale position and by depressing a needle clamp lever. When the measurement is started, it is necessary to remove the rubber band while the needle clamp lever is depressed with a finger and to read the pointed scale at predetermined intervals which are timed from the start of the measurement, when a finger is released from the clamp lever, while looking at a watch. There are problems that this operation is not only very troublesome, but also two operators are necessary to read the pointed scale and to record it while looking at a watch.

SUMMARY OF THE INVENTION

It is a principal object of the present invention to provide a rotary viscosimeter which is capable of automatically measuring the viscosity characteristics in an ultra-low fluidics range by a spring relaxation method.

It is a further object of the present invention to provide a rotary viscosimeter which is capable of performing the steady rotation viscosity measurement by constant speed rotation as well as the spring relaxation method.

In order to accomplish the above-mentioned first object, in an aspect of the present invention, there is provided: a rotary viscosimeter including a rotor which is driven to rotate while contacting with a liquid, of which a viscosity is to be measured; a rotor shaft which supports the rotor and is a first drive shaft for transmitting a rotational drive force to the rotor; rotating drive means having a drive power source for driving the rotor to rotate and an output shaft for outputting the drive power; a second drive shaft for transmitting the drive power to the rotor shaft; a first linking means for elastically linking the output shaft with the second drive shaft via the spring for transmitting the drive power therebetween; support means having a pivot and a bearing for rotatably bearing and supporting the rotor shaft; and a second linking means which bypasses the support means for linking the rotor shaft with the second drive shaft; characterized in that the viscosimeter comprises rotational angular displacement detecting means for detecting the rotational angular displacement of the rotor shaft; viscosity calculating means for calculating the viscosity from the resultant angular displacement; pivot protecting means having a locking mechanism for locking and unlocking the rotor shaft to prevent or allow rotation, respectively and a pivot separating mechanism for separating and contacting the pivot of the support means from and with the bearing, respectively; and control means for controlling the rotating drive means and the pivot protecting means; the pivot protecting means having a first state in which the rotor shaft is locked against rotating and the pivot of the support means is separated from the bearing and a second state in which the pivot of the support means is in contact with the bearing and locking of the rotor shaft is released; the control means having a control mode for measuring the viscosity by the spring relaxation method in which the control means has a capability of controlling the pivot protecting means so that the pivot protecting means is in the first state on starting and completion of the measurement and in the second state during measurement, and a capability of controlling the rotating drive means so that the torque of a spring of the first linking means reaches a preset desired value on starting the measurement.

When in the control mode for measuring the viscosity by the spring relaxation method, the control means drives the rotating drive means to adjust the torque of said spring until the spring torque attains a preset target value. If the spring has moved beyond the preliminarily set target value, the spring is relaxed to reach the target value. Upon commencment of measurement, the control means brings the pivot protecting means into the second state by driving the locking mechanism and pivot separating mechanism until the second detecting means detects that the pivot protecting means is in the second state, and then activates the viscosity calculating means.

After completion of measurement, the control means brings the pivot protecting means into the first state by driving the locking mechanism and pivot separating mechanism until the first detecting means detects that the pivot protecting means is in the first state.

Such a structure enables the automatic performing of a sequential operation such as locking of a rotor shaft, biasing of a spring, unlocking of the rotor shaft, measurement and locking of the rotor shaft after the viscosity measurement in an ultra-low fluid viscosity range by the spring relaxation method. Accordingly, troublesome manipulation such as spring winding by manual rotation of a relaxation rotor, and clamp holding with a rubber band is not needed.

In the present invention, the angular displacement of the rotor shaft is detected by angular displacement detecting means such as an angle detector and the viscosity can be calculated from the detection result. Accordingly, since reading of the angular displacement at a desired time can be automatically achieved, the number of persons involved in making a measurement can be reduced. Furthermore, it suffices for the involved operator to carry out the preparation for the measurement and to instruct to start the measurement. Since handling of the viscosimeter is easy and the amount of work involved is less, the present viscosimeter is excellent in operability. The amount of biasing is always kept constant by detecting the angular displacement and by controlling the biasing of a spring by means of the control means.

In order to accomplish the second object in a second aspect of the present invention, there is provided a rotary viscosimeter in which the control means further has a control mode for measuring the viscosity by rotating the rotor at a constant speed in which the control means has a capability of controlling the pivot protecting means so that the pivot protecting means is in the first state after the completion of measurement and in the second state from the start to the completion of measurement, and a capability of controlling the rotating drive means so that the rotating drive means drives the second drive shaft to rotate from the start to the completion of measurement.

When in the control mode for measuring the viscosity by rotating the rotor at a constant speed, the control means brings the pivot protecting device into the second state by driving the locking mechanism and pivot separating mechanism until the second detecting means detects that the pivot protecting means is in the second state, after receiving an instruction to start the measurement, and then drives the rotating drive means.

The control means stops the rotation of the rotating drive means after receiving an instruction to complete measurement and brings the pivot protecting means into the first state by driving the locking mechanism and pivot separating mechanism until the first detecting means detects that the pivot protecting means is in the first state.

In yet another aspect of the invention the control means is capable of selectively operating in either one of the control mode for measuring the viscosity by the spring relaxation method and the control mode for measuring the viscosity by rotating the rotor at a constant speed, in response to a mode selecting signal.

BRIEF DESCRIPTION OF THE DRAWINGS

FIG. 1A is a longitudinal sectional view showing the structure of an embodiment according to a preferred rotary viscosimeter of the present invention;

FIG. 10 is a flow chart showing the viscosity measuring operation using the spring relaxation method in the above mentioned embodiment;

FIG. 11 is a flow chart showing the viscosity measuring operation by rotating the rotor at a constant speed in the above mentioned embodiment;

DETAILED DESCRIPTION OF THE PREFERRED EMBODIMENTS

Preferred embodiments of the present invention will now be described with reference to relevant figures. It is to be understood that the present invention is not limited to only these embodiments.

Figure 1B:
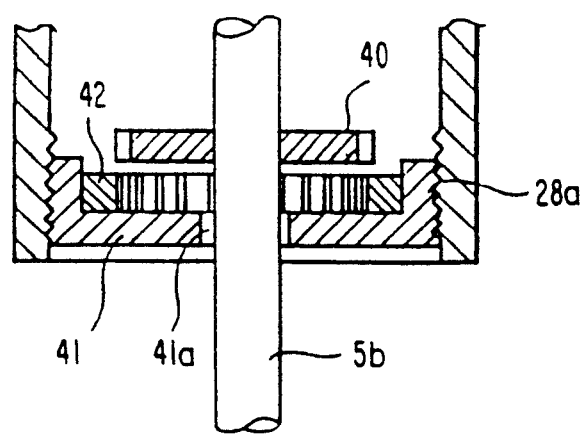
FIG. 1B is an enlarged sectional view of a part of FIG. 1A.

An embodiment of a rotary viscosimeter of the present invention is shown in FIG. 1A. The structure of a part of the embodiment is shown in FIG. 1B.

As shown in FIG. 1A, the rotary viscosimeter of the present invention comprises a plate 7a for holding sample liquid; a jacket 17 which surrounds the plate 7a for keeping the sample liquid at a constant temperature; a cone-shaped rotor 6a; a rotor shaft 5b (a first driving shaft) for holding and rotating the rotor 6a; a main body 100 for driving the rotor 6a through the rotor shaft 5b and for measuring the viscosity; and a pivot protecting device 200 which forms pivot protecting means between the main body 100 and the rotor 6a.

The main body 100 includes a driving motor 21, a rotary coupling 25 and an output shaft 22, which form rotary driving means; a second driving shaft 5c having a lower end which is linked with the rotor shaft 5b within the pivot protecting device 200; a first linking means 400 which elastically links the output shaft 22 with the second drive shaft 5c; and a rotary differential transformer 23 which functions as angular displacement detecting means between the output shaft 22 and the second drive shaft 5c.

The first linking means 400 includes a L-shaped member 4b having one end which is connected with the vicinity of the lower end of the output shaft 22; and a spiral spring 4a disposed between the other end of the L-shaped member 4b and the second drive shaft 5c. The first linking means 400 further includes an arm member 4d having one end linked with the L-shaped member 4b and the other end linked with a sleeve 10b which will be described hereafter for transmitting the rotational drive force of the output shaft 22 to the sleeve 10b.

A pin 13a which is rotatably inserted into holes (not shown) provided at respective end faces of the output shaft 22 and the second drive shaft 5c for preventing the second drive shaft 5c from swinging is provided between the output shaft 22 and the second drive shaft 5c. The holes (not shown) provided at respective end faces of the output shaft 22 and the second drive shaft 5c have such a depth that a slight axial displacement of the pin 13a is allowed, i.e. a depth by which the axial displacement of the point 13a corresponding to that of the rotor shaft 5b and the second drive shaft 5c can be absorbed.

The pivot protecting device 200 includes a pivot 11 and a bearing 12 which form means for rotatably bearing and supporting the rotor shaft; a channel-type linkage member 10a which functions as a second linkage means for linking the rotor shaft 5b with the second drive shaft 5c by bypassing the pivot 22 and the bearing 12; a locking mechanism and a pivot separating mechanism functioning as pivot protecting means, which will be described hereafter; limit switches 31 and 32 functioning as first and second detecting means for detecting the state of the pivot protecting means, and an L-shaped fitting 30 for operating the limit switches 31 and 32. Most of these components are housed in a casing 27.

The pivot 11 is mounted on the lower end of the second drive shaft 5c while the bearing 12 is mounted on a lower side 10d of a channel type member 10c provided around the second drive shaft 5c. The pivot 11 and the bearing are coaxially mounted. The sleeve 10b is rotatably supported by an upper flange 27a of the casing 27. The arm member 4d is linked with the upper end of the sleeve 10b as mentioned above.

A sleeve 28 is axially movable disposed within the casing 27 as shown in FIGS. 1A and 1B. The sleeve 28 is provided with an internal thread 28a in the lower portion thereof. The internal thread 28a is threadably meshed with a disc 41. The disc 41 is provided with a through-hole 41a in the center thereof, through which the rotor shaft 5b can freely pass. The disc 41 is provided with a first engaging member, such as an internal threaded gear 42 on the upper side thereof. The rotor shaft 5b is provided with a second engaging member, such as an externally threaded gear 40, which is meshed with the internally threaded gear 42.

When the internally threaded gear 42 is displaced by the axial displacement of the sleeve 28, the externally threaded gear 40 is brought into mesh with the internally threaded gear 42 and then contact with the displaced disc 41. Then, the externally threaded gear 40 is secured to the rotor shaft 5b so that the gear 40 is axially displaced together with the rotor shaft 5b.

A block 33 provided with a screw hole 33a is secured to the upper portion of the sleeve 28. A locking motor 34 is disposed on the flange 27a in a position opposite to the block 33. The motor 34 is provided with a threaded shaft 34a as an output shaft. The threaded shaft 34a is meshed with a screw hole 33a of the block 33. The locking motor 34 rotates the screw shaft clockwise or counterclockwise 34a to displace the block 33 upwards or downwards. The sleeve 28 is displaced in an axial direction by the axial displacement of the block 33.

The stroke of the displacement of the sleeve 28 is preset to a value which is necessary to separate the pivot 11 from the bearing 12. The stroke is preset to such a length that the externally threaded gear 42 is displaced to engage with the externally threaded gear 40 and the disc 41 is brought into contact with the externally threaded gear 40 to push the gear 40 upward for separating the pivot 11 from the bearing 12. One side of the L-shaped fitting 30 is secured to the upper portion of the sleeve 28. The L-shaped fitting 30 is disposed in such a manner that the other side 30a projects outside of the sleeve 28 and is positioned between the limit switches 31 and 32 which have been described. In other words, the side 30a is disposed so that it may be displaced by the axial displacement of the sleeve 28 for operating the limit switches 31 and 32 at the upper and lower limits of the displacement, respectively. Accordingly, the limit switches 31 and 32 are disposed in such a spaced relationship corresponding to the stroke displacement of the sleeve 28 including the driving stroke of any one of the switches.

Figure 2:
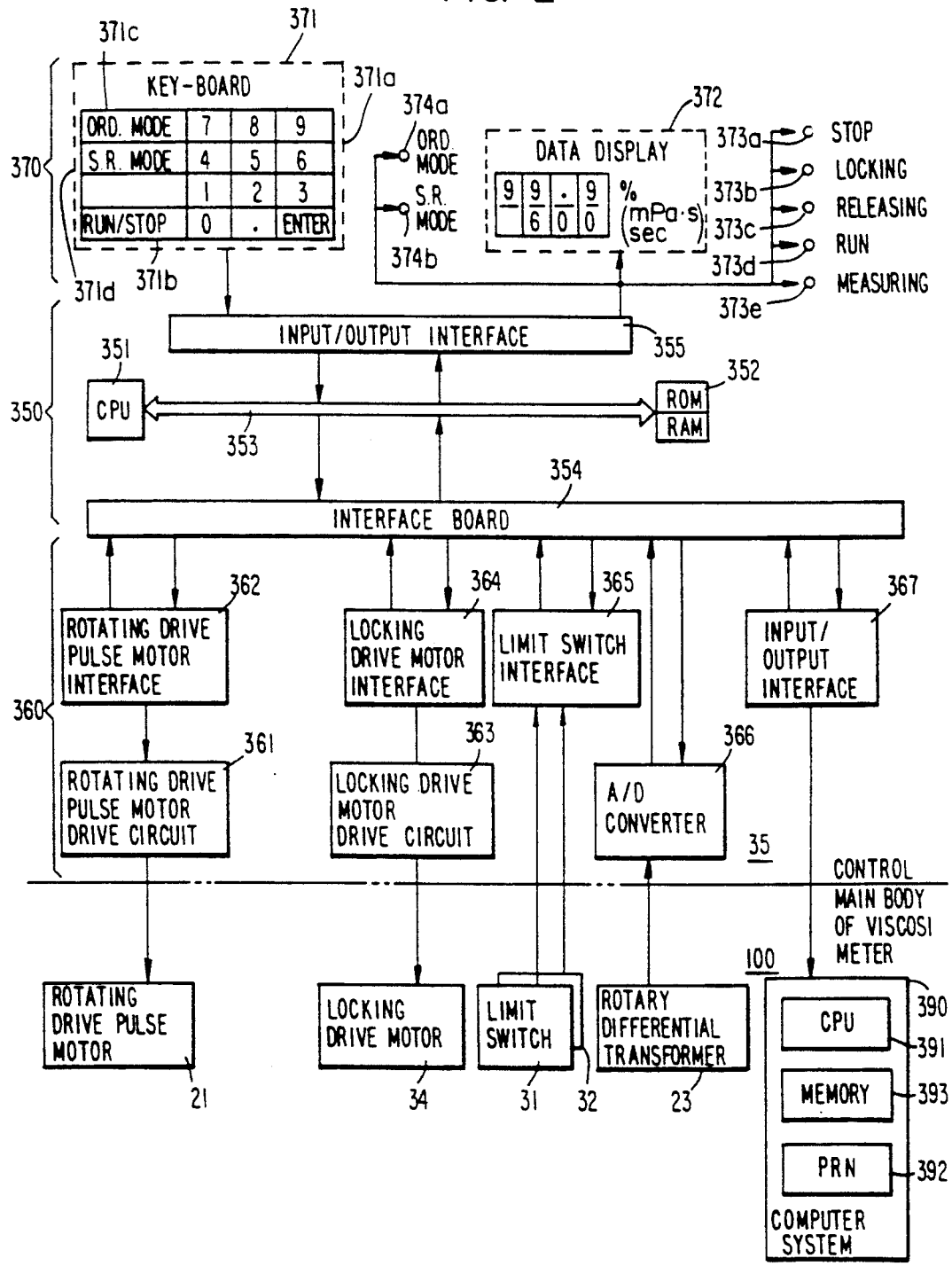
FIG. 2 is a block diagram showing the system configuration of a control system of the embodiment.

A control device 35 is formed as shown in, for example, FIG. 2. The control device 35 shown in FIG. 2 includes a drive control unit 360 which is connected with a main body 100 of the viscosimeter for transmitting and receiving measurement data and control signals; an information processing unit 350 for processing measurement data from the drive control unit 360 and for controlling the operation of a drive control system; and an input/output unit 370 for inputting/outputting information to and from the information processing unit 350.

The information processing unit 350 includes a central processing unit (CPU) for executing control for the measurement of viscosity and executing the processing of the measurement data; a memory for storing therein programs which are executed by the CPU 351, various data, results of processing; a data bus 353, and an interface board (IB) 354 for controlling input/output of the measurement data and control signals; and an input/output interface 355.

The memory 352 has a ROM (read only memory) for mainly storing programs, and a RAM (random access memory) for storing data. Some of the stored programs execute, for example, a process described below.

A process for measuring the viscosity by a spring relaxation method comprises the steps of:

accepting an instruction to start measurement in a control mode for measuring the viscosity by the spring relaxation method;

presetting the biasing condition of the spring so that the torque becomes a preliminarily preset desired value by driving the rotary driving means when detecting that the pivot protecting means is in the first state;

bringing the pivot protecting means into a second state by driving the locking mechanism and the pivot separating mechanism until a second detecting means detects that the pivot protecting means in the second state;

activating a viscosity calculating means to execute the viscosity measurement when detecting that the pivot protecting means in the second state; and bringing the pivot protecting means into the first state by driving the locking mechanism and pivot separating mechanism until the first detecting means detects that the pivot protecting means in the first state after completion of the measurement.

A process for measuring the viscosity by rotating a rotor at a constant speed comprises the steps of:

accepting an instruction to start the measurement in a control mode for measuring the viscosity by rotating a rotor at a constant speed;

driving the locking mechanism and the pivot separating mechanism in response to the instruction until the second detecting means detects that the pivot protecting means in the second state;

stopping the locking mechanism and the pivot separating mechanism to drive rotating drive means when the second detecting means detects that the pivot protecting means in the second state;

accepting an instruction to complete the measurement, which is inputted from an external device;

stopping driving of the rotating drive means in response to the instruction; and driving the locking mechanism and the pivot separating mechanism until the first detecting means detects that the pivot protecting means in the first state.

These processes are illustrated in more detail in, for example, FIGS. 3, 10, 11, 12 and 13 by reference to which the present invention will be described further.

The drive control unit 360 comprises a rotating drive motor driving circuit 360 for rotating the rotating drive motor 21; a rotating drive motor interface 362 for outputting a control signal from the information processing unit 350 to the drive circuit 361; a locking motor drive circuit 363 for driving the locking motor 34; a locking motor interface 364 for outputting a control signal from the information processing unit 350 to the locking motor drive circuit 363; a limit switch interface 365 for inputting on/off signals for the limit switches 31 and 32 to the information processing unit 350; an A/D converter 366 for analog/digital converting the measurement value of a rotary differential transformer 23 to send the converted value to the information processing unit 350; and an input/output interface 367 for connecting this control device with an external system, for example, a computer system. The computer system 390 includes, for example, a central processing unit (CPU) 391, a printer 392, a memory 393, etc.

The input/output unit 370 has a key-board 371 for externally inputting instructions to execute/stop as well as data to the control device 35, a data display 372 for displaying information outputted from the information processing unit 350, a status indicator 373 and a motor indicator 374.

The key-board 371 includes a numerical keypad 371a for inputting numerals; a run/stop switch 371b to instruct run or stop; and mode selecting keys 371c and 371d. The mode selecting key 371c selects an ordinary viscosity measurement mode (ORD MODE) in which the rotor is rotated at a constant speed, and the key 371d selects a viscosity measurement mode (S.R.MODE) in which the spring relaxation method is carried out.

The measured viscosity and the rotational speed of the rotor are displayed in numerical form on the data display 372.

Five indicators 373a to 373e are disposed in the status indicator 373. These indicators include, for example, light emitting diodes. The indicators 373a, 373b, 373c, 373d and 373e indicate STOP, LOCKING, RELEASING, RUN and MEASURING, respectively, and are illuminated depending upon the state of the viscosimeter.

The mode indicator 374 has an ordinary viscosity measuring mode indicator (ORD. MODE) 374a indicating the mode in which the rotor is rotated at a constant speed and a viscosity measuring mode indicator (S.R.MODE) 373b indicating the mode in which the spring relaxing method is carried out.

The pivot protecting device 200 has at least a first state in which the rotor shaft 5b is locked and the pivot 11 is separated from the bearing 12 and a second state in which the pivot 11 is in contact with the bearing 12 and locking of the rotor shaft 5b is released. The control system 35 controls the driving of the locking motor 34 to bring the pivot protecting device 200 into a target state and controls the driving of the rotating driving motor 21 depending upon the target state.

Operation of the present embodiment will now be described with reference to FIGS. 3, 9A, 9B, 10, 11, 12 and 13 as well as the above mentioned drawings.

Figure 9A:
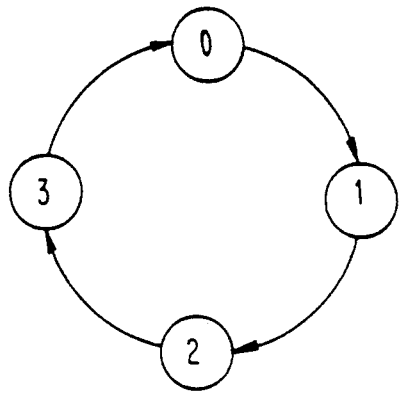
FIG. 9A is a state transition diagram showing the constant rotation measurement operation in the viscosimeter of the above mentioned embodiment.
Figure 9B:
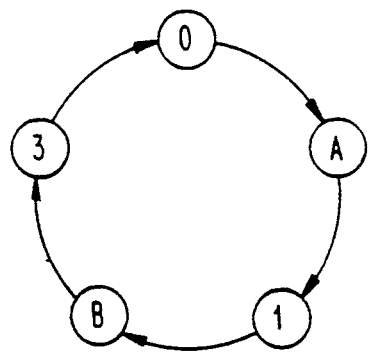
FIG. 9B is a state transition diagram of the measurement operation using the spring relaxation method in the viscosimeter of the above mentioned embodiment.

The rotary viscosimeter of the present embodiment changes its state in accordance with a series of sequences as shown in FIGS. 9A and 9B. In FIGS. 9A and 9B, a numeral "0" denotes a stopped state of the viscosimeter. At this time, the pivot 11 is separated from the bearing 12 and the rotor shaft 5b is locked against rotation. This state is referred to as a first state. A numeral "1" denotes a state in which the locking of the rotor shaft 5b is released. A numeral "2" denotes a state in which the viscosimeter is in the rotation state for measurement. In this case, the pivot 11 is in contact with the bearing 12 so that the rotor shaft 5b is released from locking. This state is referred to as a second state. A numeral "3" denotes the state in which the rotor shaft 5b is locked against rotating. A character "A" in FIG. 9B denotes that the viscosimeter is in a spring winding/rewinding operation state. A character "B" denotes that the viscosimeter is in a spring relaxing measuring state.

The sequential operation will now be described.

The summary of the measuring operation of the viscosimeter of the present embodiment will now be described with reference to FIG. 3.

When the power of the control system 35 is turned on for starting the measurement (step 1001), the CPU 351 checks whether or not the contacts of the limit switch 31 are turned on (step 1002). This can be detected by a signal from the limit switch interface 365. If the limit switch 31 is turned off, the locking motor drive circuit 363 is instructed to drive the locking motor 34 in such a direction as to lift up the sleeve 28 via the locking motor interface 364 (step 1003). At this time, the CPU 351 lights the indicator 373b until the limit switch 31 is brought into a conductive state. If the limit switch 31 is already turned on, the locking motor 34 is not driven.

Figure 8A:
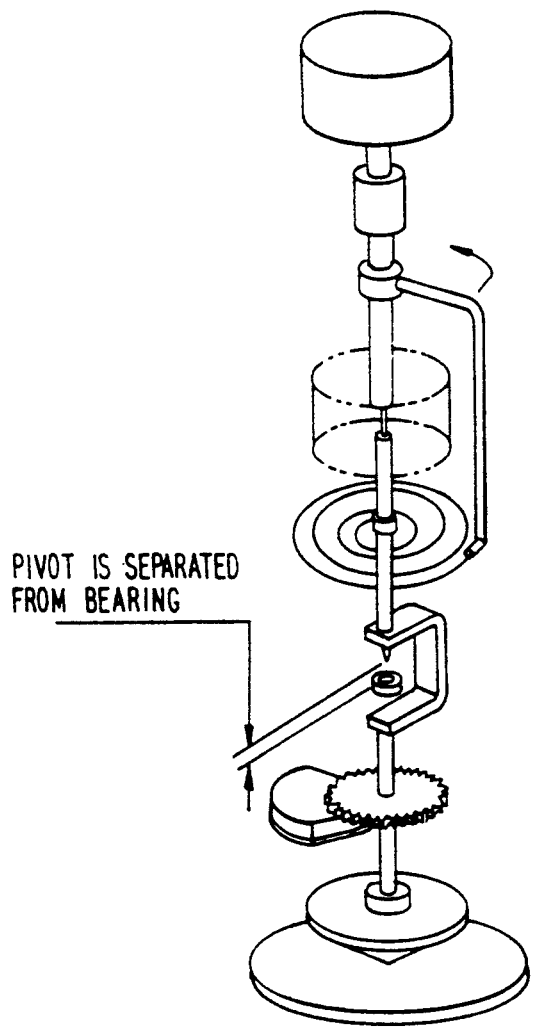
FIG. 8A is an explanatory view showing the state in which the pivot is separated from the bearing and the rotor shaft is locked in the rotary viscosimeter of the present invention.

When the locking motor 34 is driven, the screw 34a is rotated. The block 33 which is meshed with the screw 34a is axially displaced by the rotation of the screw 34a so that the sleeve 28 to which the block 33 is secured is moved upward. When the sleeve 28 is moved upward, the disc 41 to which the sleeve 28 is secured is also moved upward. The internally threaded gear 42 which is provided on the disc 41 is brought into threadable engagement with the externally threaded gear 40 secured to the disc 41 by the upward movement of the disc 41. This causes the rotor shaft 5b to be locked against rotation by the sleeve 28. Further upward movement of the sleeve 28 causes the disc 41 to push up the externally threaded gear 40. This causes the rotor shafts 5b and 5c to be pushed upward for moving the pivot 11 upward so that the pivot 22 is separated from the bearing 12. This state is shown in FIG. 8A.

This operation causes the rotor shaft 5b to be locked and causes the pivot 11 to be separated from the bearing 12. The locking of the rotor shaft 5b and separation of the pivot 11 from the bearing 12 is also performed on completion of measurement as will be described hereafter.

Then, determination of the measuring mode is made (step 1004). Measuring mode determination is made by checking which of the mode selecting keys 371c and 371d is selected. If the spring relaxation method is selected, the spring relaxation viscosity measurement method is carried out (step 1005). If the viscosity measurement by the constant speed rotation method is selected, this measurement method is carried out (step 1007). When respective measurements are completed, respective completion operations are carried out (steps 1006 and 1008) to complete measuring operation.

Now, the viscosity measuring operation using the spring relaxation method will be described with reference to the flow chart of FIG. 10.

An input instruction to execute measurement is accepted (step 1501). If execution is instructed, the CPU 351 accepts this instruction and presets the spring 4a into a biasing state at a target peak value. Since the rotor shaft 5b is locked in this state, the spring 4a is wound or rewound to change the biasing state if the rotating drive pulse motor 21 is driven to rotate.

In the measurement relying on the spring relaxation method of the present embodiment, the winding speed of the spring is not directly related with measurement. However, in order to reduce variations in position where the spring is stopped on completion of winding, a low winding speed is selected. For example, the winding speed may be practically about 5 rpm. The speed of the pulse motor 21 can be changed depending upon the instruction. The speed can be changed by changing, for example, the pulse rate of a pulse train drive signal. Instruction of the speed can be made, for example, by feeding a speed instruction based on the speeds preliminarily registered in the RAM to the rotating drive motor drive circuit 361 by the CPU 351. Alternatively, the rotating drive motor drive circuit 361 may be provided with the capability of instructing the speed presetting.

On adjustment of the biasing state of the spring, the winding angle $\theta$ of the spring is detected by the rotary differential transformer 23 is converted into a digital value by the A/D converter 366 and is sent to the CPU 351. The CPU 351 compares the winding angle $\theta$ of the spring with the target peak value $\Theta$ (step 1502) and activates the rotating drive pulse motor drive circuit 361 depending upon the result of the comparison for controlling the rotation of the rotating drive pulse motor 21. If $\theta > \Theta$, the spring 4a is wound beyond the target value. Accordingly, the pulse motor 21 is reversed to rewind the spring 4a (step 1503). If $\theta < \Theta$, the spring 4a is not wound to the desired value. Accordingly, the pulse motor 21 is normally rotated to wind the spring 4a to the desired value (step 1504).

The target peak value $\Theta$ can be inputted by using, for example, the numerical keypad 371a of the key-board. The input value is stored in, for example, the RAM together with mode selecting information. The CPU 351 executes various determinations with reference to the information in the RAM.

If $\theta > \Theta$, the spring 4a may be wound to obtain the target peak value after the spring 4a has been completely rewound. Alternatively, the spring 4a may be automatically rewound after completion of measurement.

If $\theta = \Theta$, the CPU 351 does not drive the pulse motor 21 and activates the locking drive motor drive circuit 363 for driving the locking drive motor 34 in a releasing direction (step 1506). The CPU 351 continues this releasing operation until the limit switch 32 is turned on (step 1507) and lights the indicator 373c.

Figure 8B:
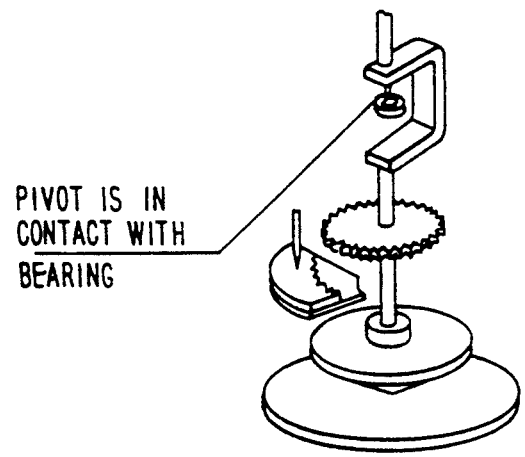
FIG. 8B is an explanatory view showing the state in which the pivot is in contact with the bearing and the rotor shaft is released in the rotary viscosimeter of the present invention.

In other words, the locking drive motor 34 is driven to lower the sleeve 28 in the releasing operation which is opposite to the locking operation. When the locking motor is driven, the screw 34a is rotated. The block 33 which is meshed with the screw 34a is axially displaced by the rotation of the screw 34a so that the sleeve 28 to which the block 33 is secured is lowered. When the sleeve 28 is lowered, the disc 41 which is secured to the sleeve 28 is lowered. The externally threaded gear 40 which has been pushed up by the disc 41 is lowered by the lowering of the disc 41 so that the pivot 11 is lowered make to contact with the bearing 12. The internally threaded gear 42 is disengaged from the externally threaded gear 40 so that locking of the rotor shaft 5b by the sleeve 28 is released. This state is shown in FIG. 8B.

When the limit switch 32 is turned on, the releasing operation is stopped to carry out the spring relaxation measurement. At this phase, the rotor shaft 5b is rotatable as shown in FIG. 8B and the pivot 11 is in contact with the bearing 12. In this measurement, the rotor 6a is driven by the relaxation torque exerted by the spring 4a to rotate against the viscosity torque of the sample liquid. This rotation is detected by the rotary differential transformer 23. The CPU 351 samples at a predetermined period the rotational angular displacement data as spring relaxation data which is obtained form the rotary differential transformer 23 via the A/D converter 366 (step 1508).

During this period of time, the CPU 351 compares the period of time $\tau$ lapsed since the start of measurement with the predetermined sampling period T (step 1509). If $\tau < T$, the measuring operation is continued and the indicator 373e is lit for this operation. If $t \geq T$, a measurement terminating signal is outputted to terminate the measurement (step 1510).

The sampling interval and the sampling period can be preliminarily registered by means of the key-board 371. The selected sampling interval is, for example, from 1 to several seconds. The selected sampling period is, for example, from 10 to 20 minutes. Registration can be made in the RAM of the memory 352. The lapsed period of time t can be determined, for example, by providing a timer for counting the lapsed period of time. The sampling period T may be preliminarily preset in the timer. In this case, comparison of T with t is not necessary. Measurement is terminated at the time when a terminating signal is outputted from the timer.

The spring relaxation data is stored in, for example, the RAM of the memory 352. Operation for determining the viscosity is performed based upon the stored data. A result of the operation is stored in the RAM and displayed in the data display 372.

Alternatively, the measurement data may be sent to the computer system 390 and temporarily stored in the memory 393. Operation to determine the viscosity can be performed by the CPU 391 based upon the stored data. In this case, the result can be printed out by a printer 392 of the computer system. The result can be displayed in numerical, graphical or other form on a display (not shown).

Figure 12:
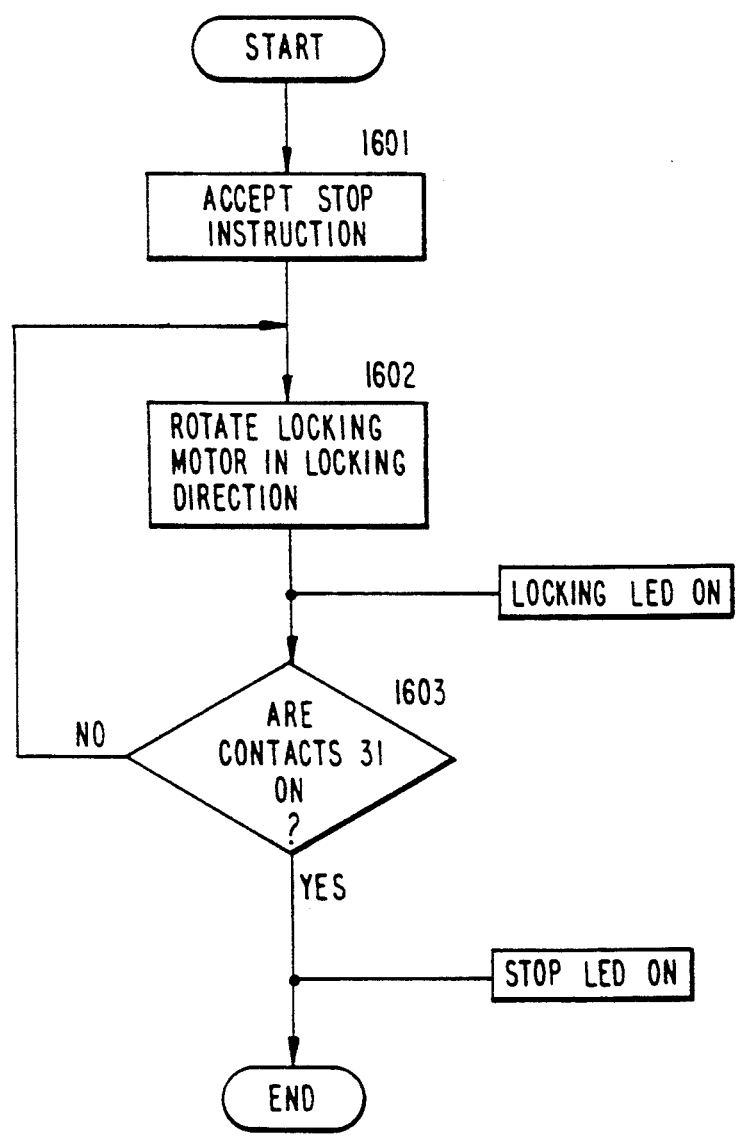
FIG. 12 is a flow chart for the completion operation in the viscosity measurement using the spring relaxation method in the above mentioned embodiment.

Thereafter, the measurement termination operation is executed. This operation begins with reception of a stop instruction as shown in FIG. 12 (step 1601). The stop instruction is made in response to the measurement termination signal when the measurement is conducted by the spring relaxation method. If the CPU 351 receives the stop instruction, the CPU 351 controls the locking drive motor drive circuit 363 to drive the locking drive motor 34 in such a direction that the rotor shaft 5b is locked, i.e. the sleeve 28 is moved upward (step 1602). This control is continued until the contacts of the limit switch 31 are turned on (step 1603). During this period of time, the indicator 373b is lit. When the limit switch 31 is turned on, driving of the locking drive motor 34 is stopped and the indicator 373a is lit.

Sequential operation of the viscosity measurement by the spring relaxation method is thus completed.

Now, operation for measuring the viscosity by the constant speed rotation method will be described with reference to the flow chart of FIG. 11.

An input instruction for measurement execution is accepted (step 170). If there is an execution instruction, the CPU 351 receives it and instructs the driving of the locking motor 34 in such a direction that the sleeve 28 is lowered (step 1702). The releasing operation is continued until the limit switch 32 is turned on. During this operation, the CPU 351 lights the indicator 373c. If the limit switch 32 is turned on, the releasing operation is stopped to light the indicator 373d (step 1703). The CPU 351 instructs the rotating drive motor drive circuit 361, via the rotating drive motor interface 362, to rotate the rotating drive motor 21 (step 1704). The rotational speed can be specified and changed as mentioned above.

Measurement of the viscosity is conducted in this state. Measurement is performed by detecting the angular displacement between the output shaft 22 and the second drive shaft 5c by means of the rotary differential transformer 23. The value detected by the rotary differential transformer 23 is converted into a digital value by the A/D converter 366 and is sent to the information processing unit 350 via the interface board 354.

The measurement data are stored in, for example, the RAM of the memory 352 and operated on by the CPU 351. The operation result is displayed on the data display 372 together with the rotational speed of the rotor which is separately determined.

Also in this case, the measurement data may be sent to the computer system 390 and temporarily stored in the memory 393. Operation for determining the viscosity by the CPU 391 may be performed based upon the stored data. The operation result can be printed out by the printer 392 of the computer system. Alternatively, it may be displayed on a display (not shown) in numerical or graphical form.

Figure 13:
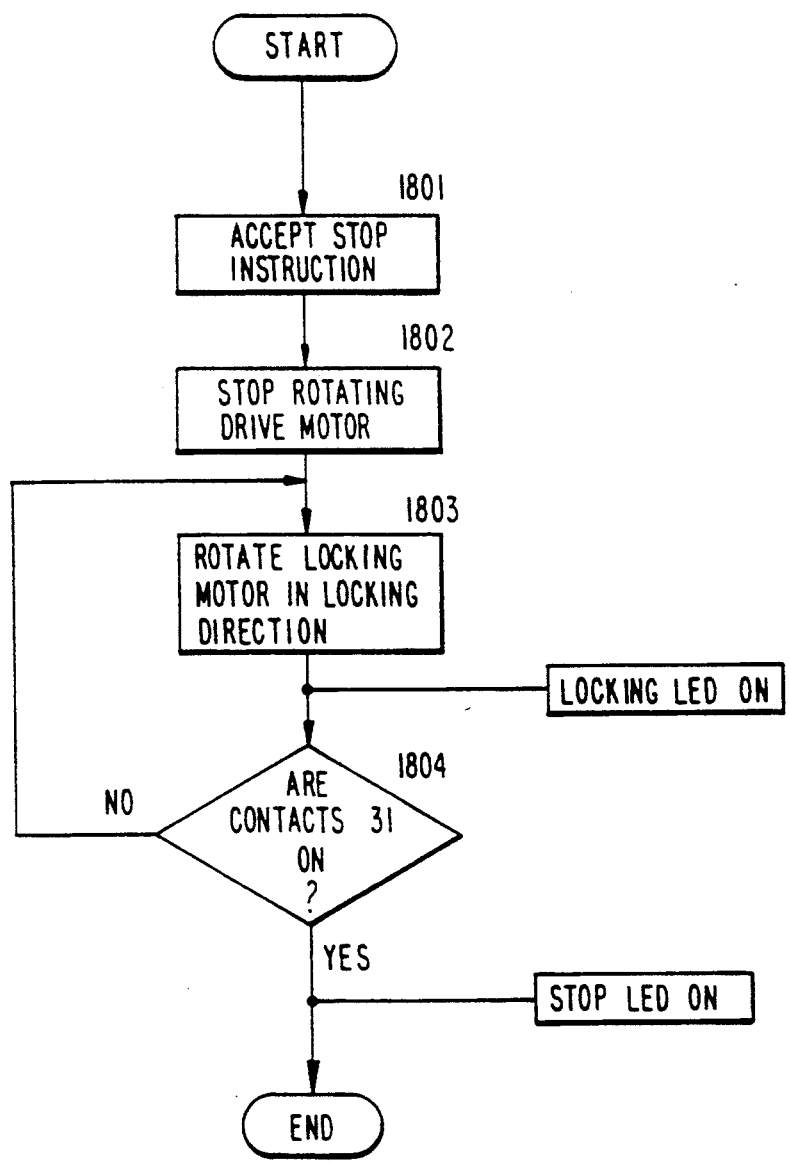
FIG. 13 is a flow chart showing the completion operation in the constant rotational speed viscosity measurement.

Operation on completion of measurement by the viscosimeter will now be described with reference to the flow chart of FIG. 13.

A stop instruction is received while the rotating drive motor is rotating and the indicator 373d is illuminated (step 1801). This stop instruction is made by input of a step operation of the run/stop switch 371b. If stop is instructed, the CPU 351 sends an instruction to the rotating drive motor drive circuit 356 via the rotating drive motor interface 362 for stopping the rotating drive motor 21 (step 1802).

The CPU 351 then instructs the locking motor drive circuit 363 via the locking motor interface 364 to drive the locking motor 34 in such a direction that the sleeve 28 is moved upward (step 1803). The locking operation is continued until the limit switch 31 is turned on. During this operation, the CPU 351 lights the indicator 373b. The CPU 351 stops the locking operation and lights the indicator 373a if the limit switch 31 is turned on (step 1804).

The series of operations for measuring the viscosity by the constant speed rotation method is thus completed.

Figure 3:
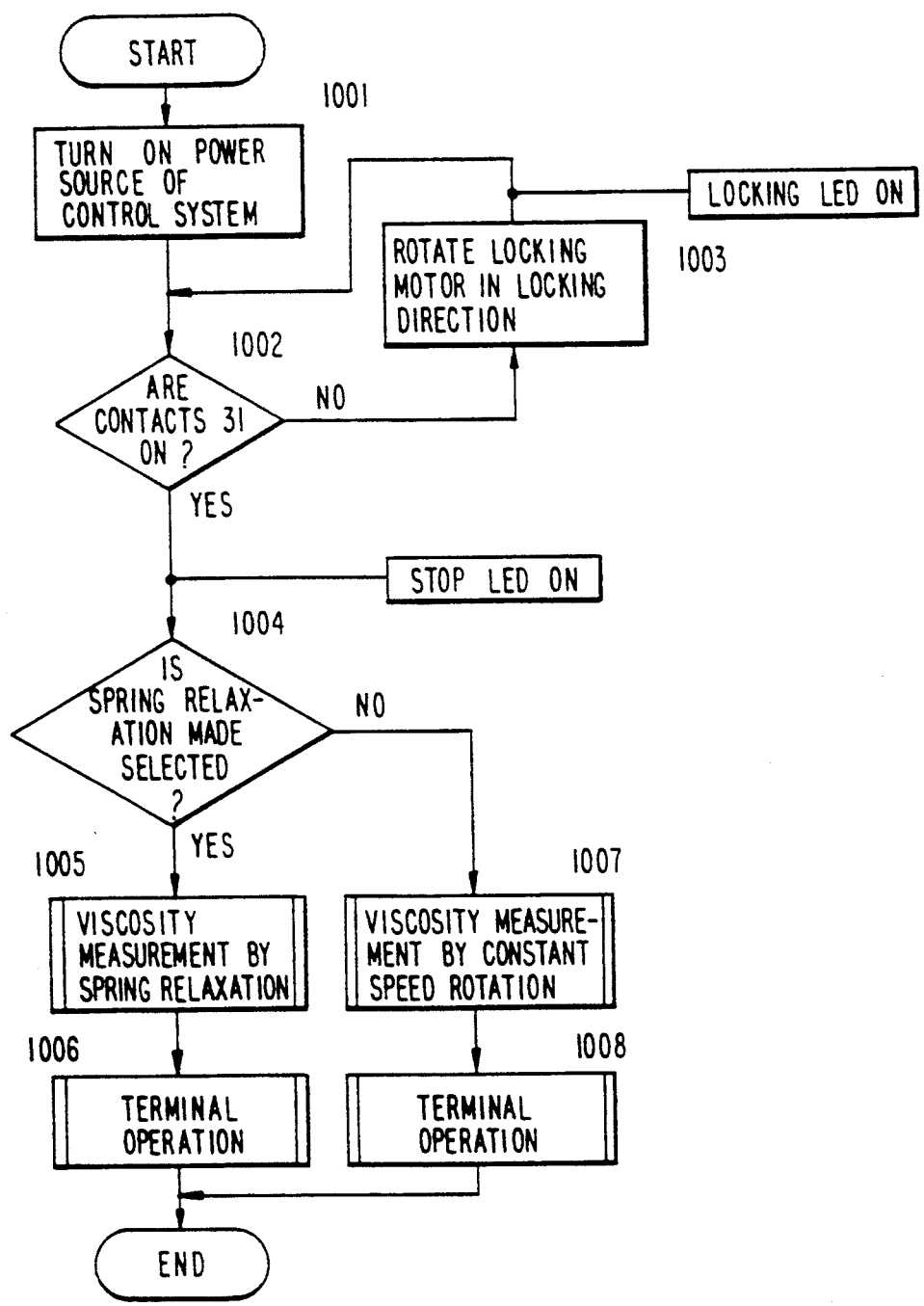
FIG. 3 is a flow chart showing the summary of the operation for measuring the viscosity in the foregoing embodiment.
Figure 4:
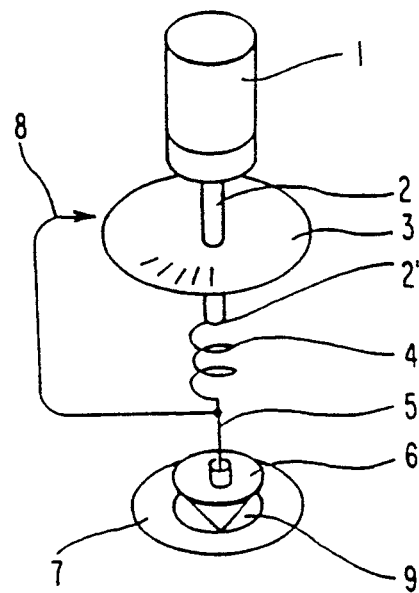
FIG. 4 is an explanatory view to explain the principle of operation of a cone plate type rotary viscosimeter.
Figure 5:
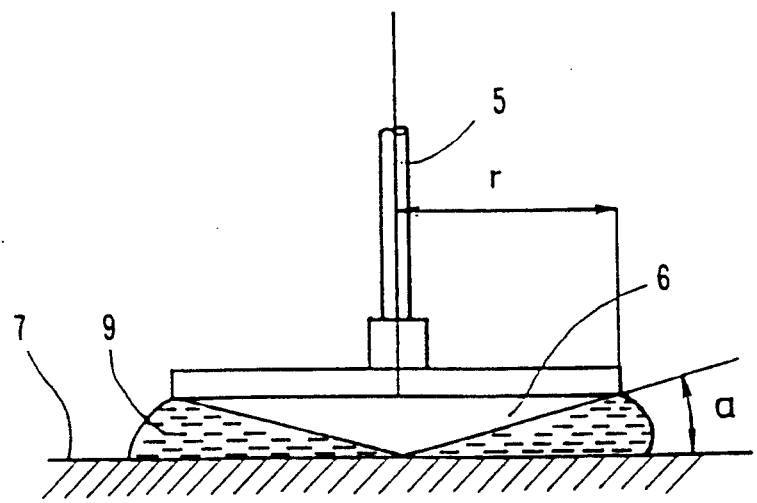
FIG. 5 is an enlarged view of a cone plate portion.
Figure 6:
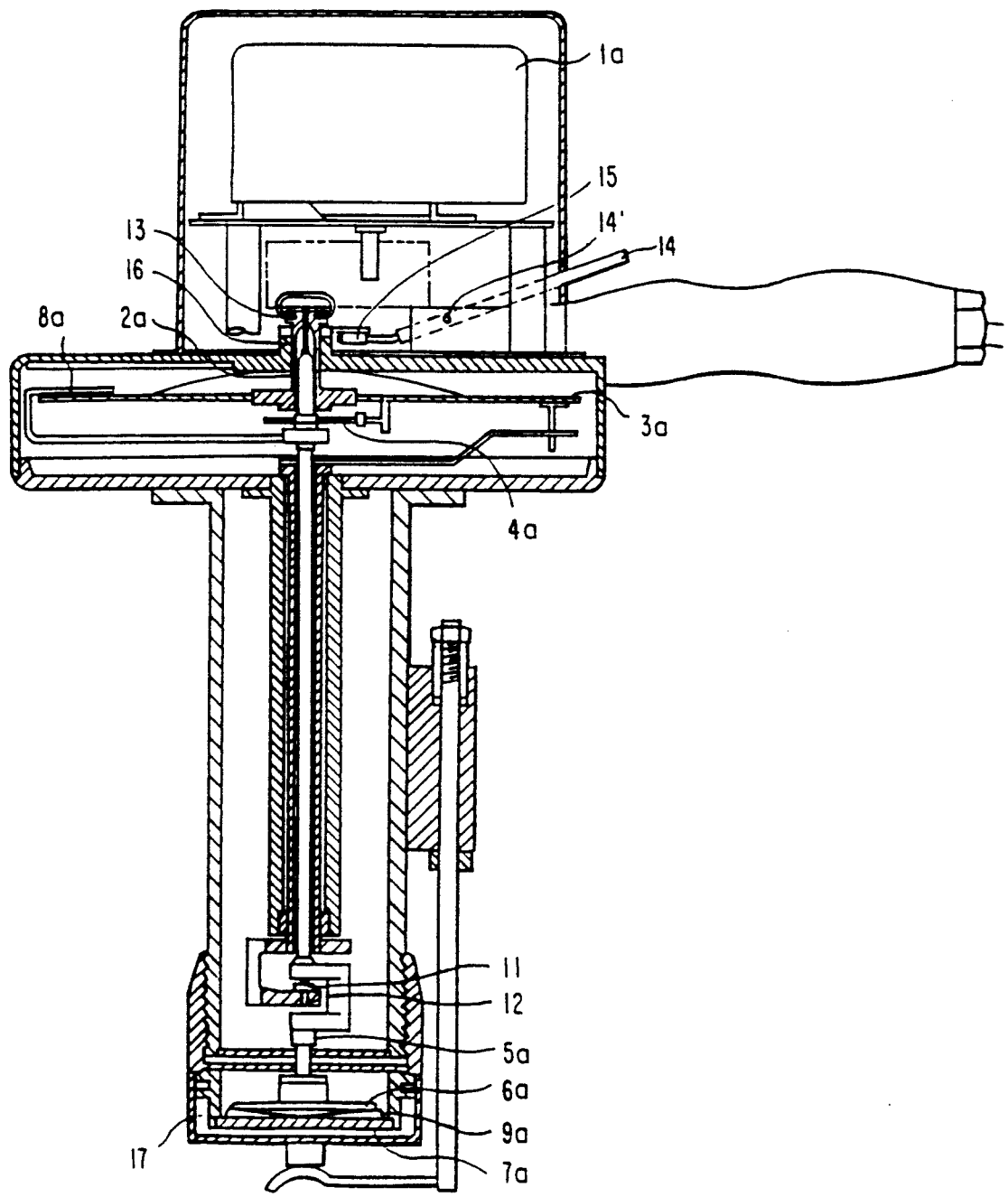
FIG. 6 is a longitudinal sectional view showing the structure of a conventional cone plate type rotary viscosimeter.
Figure 7:
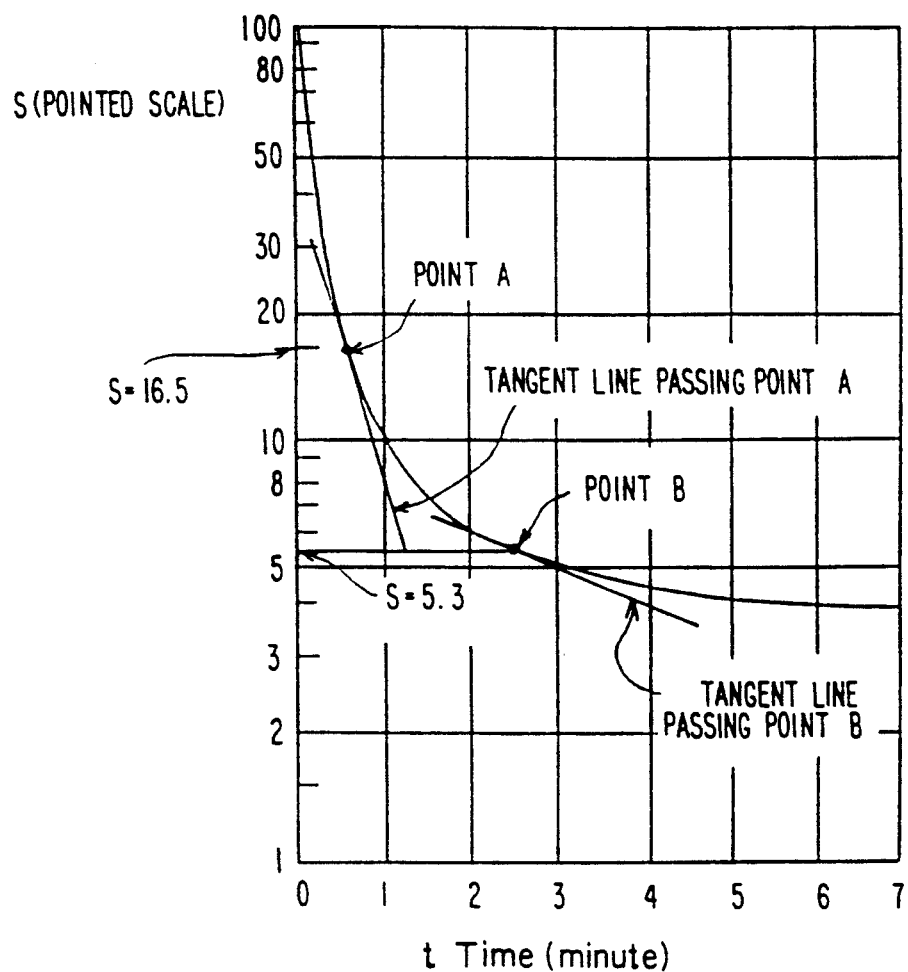
FIG. 7 is a graph showing data which are obtained by the measurement of the viscosity in an ultra-low fluid viscosity range using the spring relaxation method.

The motor shaft 5b is locked against rotation after the completion operation 1006 and 1008 shown in FIG. 3 has been performed. The pivot 11 is separated from the bearing 12. Accordingly, the pivot can be prevented from being damaged even if the rotor 6a is washed or replaced. Since the completion operation is sequentially and automatically performed in response to only one instruction of the measurement termination until the protection of the pivot, the rotor is prevented from being removed when a user fails to lock the rotor. Since the state of the viscosimeter is displayed in the present embodiment, a user can easily notice the state of operation of the viscosimeter and wrong operation can be prevented.

Since the rotating drive motor is not driven while the locking motor is driven in the present embodiment, a locking or releasing operation simultaneous with the measurement of the viscosity is prevented.

Another embodiment of the present invention will now be described with reference to FIG. 14.

Figure 14:
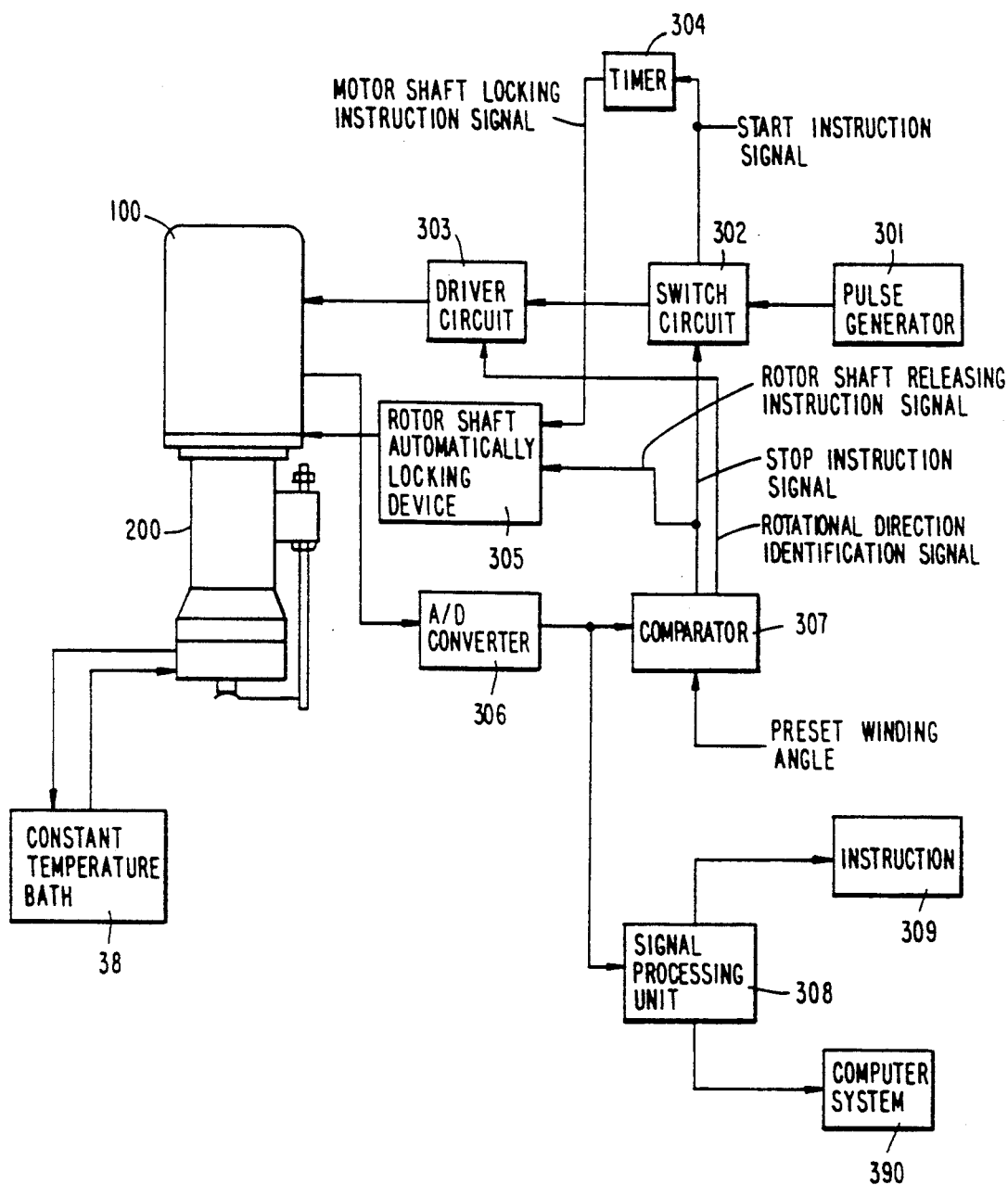
FIG. 14 is a block diagram showing the structure of another embodiment of the present invention.

The embodiment shown in FIG. 14 is a viscosimeter having a main body 100 of the viscosimeter and a pivot protecting apparatus 200 which are similar to those of the above mentioned embodiment and is identical with the above mentioned embodiment in structure and function except that the structure of a control system is different from that of the above mentioned embodiment. Accordingly, only the difference therebetween will mainly be described herein.

The control system of the present embodiment performs control by means of a hardware logic circuit while the control system of the above mentioned embodiment performs control by means of software using a computer.

In FIG. 14, the present embodiment comprises a pulse generator 301 for generating a drive signal; a sampling time timer 304 for determining a sampling time; a driver circuit 303 for driving a rotor driving motor (refer to FIG. 1A) disposed within the main body of the viscosimeter; an automatic rotor shaft locking device 305 for automatically locking a rotor shaft similarly to the embodiment of FIG. 1A; and A/D converter 306 for converting a change in rotational angle between the rotor and a drive motor, detected by a rotary difference transformer into a digital value; a comparator 307 for outputting a winding stop instruction signal and a signal identifying the rotational direction when the change in rotation angle becomes a preset winding angle; a switching circuit 302 for selecting whether or not a drive pulse from the pulse generator 301 is inputted to a driver circuit 303 in response to signals from the pulse generator 301 and the comparator 307; a signal processing unit 308 for determining the viscosity based upon the change in the rotational angle; and an indicator 309 for indicating an output from the signal processing unit 308. The signal processing unit 308 may be connected with another computer system 390. The computer system includes, for example, a CPU 391, printer 392, etc. In FIG. 14, a constant temperature bath 38 for supplying a liquid to maintain a sample liquid at a constant temperature is illustrated. This bath may be, of course, connected with the embodiment shown in FIG. 1A.

In the measurement of the viscosity in an ultra-low speed fluid range by the spring relaxation method in the present embodiment, the pivot 11 is separated form the bearing 12 and is locked against rotation, and a spiral spring 4a is wound by rotating the pulse motor 21 at a constant speed while locking the rotor shaft 5b (refer to FIG. 8A). Although the rotational speed is not directly related with the spring relaxing measurement since it is only a winding speed, this rotational speed is selected to be a low speed in order to reduce the variations in the stop position when the spring is stopped to complete winding.

As the spiral spring 4a is wound, the change in angle between an output shaft 22 and a rotor shaft 5b increases. Accordingly, the digital value which is obtained by A/D converting an output signal from an angle detector 23 is inputted into a comparator 307 to determine the difference between the digital value and a target winding value which is preliminarily manually preset by a key-switch. When this value becomes 0 upon reaching the target winding value, winding is completed by stopping the pulse motor 21 (refer to FIG. 8A). Then, by releasing the locking of the rotor shaft, the rotor 6a is driven to rotate by the relaxation torque exerted by the spiral spring 4a against the viscosity torque of the sample liquid. By processing the change in the angle, i.e. the change in indicated degree with the lapsed time since the locking of the rotor shaft is released in the signal processing unit 308, the behavior of the viscosity of the sample liquid in an ultra-low speed fluid range can be analyzed. The result of analysis can be displayed on a display 309.

After the lapse of the time preset in the sampling time timer 304, a rotor shaft locking instruction signal is generated from the timer 304 to actuate the automatic rotor shaft locking device 305. The rotor shaft 6a is thus locked so that the viscosimeter is returned to a stop state to complete measurement.

In accordance with the structure of the present invention, measurement of the viscosity for the analysis of the characteristics of the sample liquid in an ultra-low speed fluid range using the spring relaxation method is also sequentially and automatically performed except for initially charging the sample liquid into the viscosimeter.

Although the sleeve is displaced by means of the locking motor in each of the foregoing embodiments, the displacing method is not limited to this method. The displacement can be performed, for example, by using a linear motor, a solenoid, etc. as an actuator. This limit switch may be an optical switch, magnetic switch, pressure sensitive switch, etc. without being limited to a micro-switch.

The present invention is not limited to only the above-mentioned embodiments and may be embodied in any other manner so that similar functions are performed. Various changes and additions of the present invention are possible within the scope of the disclosed technical concept.

What is claimed is:

1. A rotary viscosimeter, comprising:
 a rotor which is driven to rotate while contacting with a liquid of which a viscosity is to be measured;
 a rotor shaft which supports the rotor and is a first drive shaft for transmitting a rotational drive force to the rotor;

rotating drive means having a drive power source for driving the rotor to rotate and an input shaft for outputting the drive power;

a second drive shaft for transmitting the drive power to the rotor shaft;

a first linking means for elastically linking said output shaft with the second drive shaft via a spring for transmitting the drive power therebetween;

support means having a pivot and a bearing for rotatably bearing and supporting the rotor shaft; and a second linking means which bypasses said support means for linking the rotor shaft with the second drive shaft, wherein said viscosimeter comprises rotational angular displacement detecting means for detecting a rotational angular displacement of said rotor shaft, viscosity calculating means for calculating said viscosity from the detected angular displacement, pivot protecting means having a locking mechanism for locking and unlocking the rotor shaft against and for rotating, respectively, a pivot separating mechanism for separating and contacting the pivot of said support means from and with the bearing, respectively, and control means for controlling said rotating drive means and said pivot protecting means, said pivot protecting means having a first state in which the rotor shaft is locked against rotating and the pivot of said support means is separated from the bearing and a second state in which the pivot of said support means is in contact with the bearing and locking of the rotor shaft is released; said control means having a control mode for measuring the viscosity by a spring relaxation method in which the control means controls the pivot protecting means so that the pivot protecting means is in the first and second state on starting and completion of measurement and in the second state during measurement and also controls said rotating drive means so that the torque on said spring of the first linking means reaches a preset desired value at the start of measurement.

2. The rotary viscosimeter according to claim 1, wherein said:

control means has a control mode for measuring the viscosity by rotating the rotor at a constant speed in which said control means controls the pivot protecting means so that the pivot protecting means is in the first state after the completion of measurement and in the second state from the start to the completion of measurement and also controls said rotating drive means so that said rotating drive means drives the second drive shaft to rotate from the start to the completion of measurement.

3. The rotary viscosimeter according to claim 1, wherein:

said control means is selectively operated in either one of the control mode for measuring the viscosity by the spring relaxation method and the control mode for measuring the viscosity by rotating the rotor at a constant speed, in response to a mode selecting signal.

4. The rotary viscosimeter according to claim 1, further comprising:

a first and second detecting means for detecting that said pivot protecting means is in the first and second states, respectively.

5. The rotary viscosimeter according to claim 4 wherein:

said control means controls the rotating drive means to be driven to rotate provided that said second detecting means detects that the pivot protecting means in the second state when said control means is in the control mode for measuring the viscosity by rotating the rotor at a constant speed.

6. The rotary viscosimeter according to claim 4, wherein:

said control means controls the rotating drive means to be driven to rotate provided that said first detecting means detects that the pivot protecting means in the first state when said control means is in the control mode for measuring the viscosity by the spring relaxation method.

7. The rotary viscosimeter according to claim 4, wherein:

said control means includes means for carrying out the steps of driving the rotating drive means under the condition that the first detecting means detects that the pivot protecting means is in the first state after receiving an instruction to start the measurement in the control mode for measuring the viscosity by the spring relaxation method, for adjusting the torque of said spring until the spring torque becomes a preset desired value, means for carrying out steps of bringing the pivot protecting means into the second state by driving said locking mechanism and pivot separating mechanism until the second detecting means detects that the pivot protecting means is in the second state on measurement and activating the viscosity calculating means when the second detecting means detects that the pivot protecting means is in the second state, and means for bringing the pivot protecting means into the first state by driving said locking mechanism and pivot separating mechanism until the first detecting means detects that the pivot protecting means is in the first state after completion of measurement.

8. The rotary viscosimeter according to claim 7, further comprising:

display means for displaying an operation state of the viscosimeter.

9. The rotary viscosimeter according to claim 4, wherein:

said control means includes means for carrying out the steps of bringing the pivot protecting device into the second state by driving said locking mechanism and pivot separating mechanism until the second detecting means detects that the pivot protecting means is in the second state after receiving an instruction to start the measurement in the control mode for measuring the viscosity by rotating the rotor at a constant speed and for driving the rotating drive means when the second detecting means detects that the pivot protecting means is in the second state, and means for stopping the rotation of the rotating drive means after receiving an instruction to complete measurement and for bringing the pivot protecting means into the first state by driving said locking mechanism and pivot separating mechanism until the first detecting means detects that the pivot protecting means is in the first state.

10. The rotary viscosimeter according to claim 9, further comprising:
   display means for displaying an operation state of the viscosimeter.

11. The rotary viscosimeter according to claim 1, wherein:
   first linking means includes a spiral spring for elastically linking said rotating drive means with the second drive shaft.

12. The rotary viscosimeter according to claim 1, wherein:
   the angular displacement detecting means includes a rotary differential transformer for electrically detecting the angular displacement.

13. The rotary viscosimeter according to claim 1, wherein:
   the the control means controls said rotating drive means so that the torque of the spring of the first linking means on starting of measurement includes both increasing and decreasing of the torque of the spring beyond a current value.

* * * * *

UNITED STATES PATENT AND TRADEMARK OFFICE
CERTIFICATE OF CORRECTION

PATENT NO.  : 5,287,732
DATED       : February 22, 1994
INVENTOR(S) : Koji SEKIGUCHI It is certified that error appears in the above-indentified patent and that said Letters Patent is hereby corrected as shown below:

Column 1, line 11, change "viscosity" to --shear rate--;
Column 1, line 16, change "viscosity" to --shear rate--;
Column 5, line 64, change "viscosity" to --shear rate--;
Column 7, line 3, change "viscosity" to --shear rate--;
Column 17, line 37, delete "and second";
Column 18, line 28, after "out" insert --, at the start of measurement,--
Column 18, line 32, delete "on";
Column 18, line 33, delete "measurement".

Signed and Sealed this

Twenty-fourth Day of October, 1995

*Attest:*

BRUCE LEHMAN

*Attesting Officer*   *Commissioner of Patents and Trademarks*